United States Patent
Goloubev et al.

(10) Patent No.: US 10,646,169 B2
(45) Date of Patent: May 12, 2020

(54) PROCESS OF CONTROLLING A DEVICE FOR DIAGNOSING AND MONITORING INDIVIDUAL ACTIVITY, CONDITIONS, AND DIET

(71) Applicants: Mikhail Goloubev, Baltimore, MD (US); Lethia Jackson, Ellicott City, MD (US); Julisha Patten, Apollo Beach, FL (US)

(72) Inventors: Mikhail Goloubev, Baltimore, MD (US); Lethia Jackson, Ellicott City, MD (US); Julisha Patten, Apollo Beach, FL (US)

(*) Notice: Subject to any disclaimer, the term of this patent is extended or adjusted under 35 U.S.C. 154(b) by 141 days.

(21) Appl. No.: 15/990,574

(22) Filed: May 25, 2018

(65) Prior Publication Data
US 2019/0357856 A1    Nov. 28, 2019

(51) Int. Cl.
| | | |
|---|---|---|
| A61B 5/00 | (2006.01) | |
| G16H 40/63 | (2018.01) | |
| A61B 5/11 | (2006.01) | |
| A61B 5/0205 | (2006.01) | |
| A61B 5/021 | (2006.01) | |
| A61B 5/024 | (2006.01) | |

(52) U.S. Cl.
CPC .......... *A61B 5/7282* (2013.01); *A61B 5/0002* (2013.01); *A61B 5/0205* (2013.01); *A61B 5/1118* (2013.01); *A61B 5/4866* (2013.01); *A61B 5/7225* (2013.01); *A61B 5/7275* (2013.01); *A61B 5/742* (2013.01); *A61B 5/746* (2013.01); *G16H 40/63* (2018.01); *A61B 5/021* (2013.01); *A61B 5/02438* (2013.01)

(58) Field of Classification Search
CPC .... A61B 5/00; A61B 5/01; A61B 5/02; A61B 5/04; A61B 5/05; A61B 5/08; A61B 5/11; A61B 5/14; A61B 5/16; A61B 5/48; A61B 5/68; A61B 5/72; A61B 5/74; A61B 2562/02; A61B 2560/02; A61B 2576/00; A61B 2503/10
USPC ...................................................... 600/301
See application file for complete search history.

(56) References Cited

U.S. PATENT DOCUMENTS

| | | | | |
|---|---|---|---|---|
| 2008/0214903 A1* | 9/2008 | Orbach | ............... | A61B 5/486 600/301 |
| 2010/0217099 A1* | 8/2010 | LeBoeuf | ............... | A61B 5/486 600/301 |
| 2013/0171599 A1* | 7/2013 | Bleich | ............... | G09B 19/00 434/247 |

\* cited by examiner

*Primary Examiner* — William J Levicky
*Assistant Examiner* — George E Banis

(57) ABSTRACT

Scrupulous mathematical analysis of officially recognized results of approved medical research had allowed to establish dependence of personal heart beats on individual metabolic rate related to the person's weight, height, age, gender, medical treatment, blood pressure, as well as heart rate at rest, and led to deriving a process for a device continuously converting personal pulse into trustworthy estimates of instantaneous physical or mental stress, blood pressure, and metabolic, instead of uncertain mechanical, energy.

1 Claim, 2 Drawing Sheets

PROCESS OF CONTROLLING A DEVICE FOR DIAGNOSING AND MONITORING INDIVIDUAL ACTIVITY, CONDITIONS, AND DIET

U.S. PATENT DOCUMENT

| | | | |
|---|---|---|---|
| 5,810,736 B1 | September 1998 | Pail | 600/500 |
| 5,807,267 D1 | September 1998 | Bryars et al. | 600/500 |
| 6,095,984 B1 | August 2000 | Amano et al. | 600/500 |
| 9,597,004 B2 | March 2017 | Hughes et al. | A61B 5/0468 (20130101) |
| 6,580,942 B1 | June 2003 | Willshire | 600/509 |
| 9,566,007 B2 | February 2017 | McCombie et al. | A61B 5/0205 (20130101) |
| 6,042,549 B1 | March 2000 | Amano et al. | 600/500 |
| 9,566,010 B2 | February 2017 | Chu | A61B 5/02438 (20130101) |
| 9,430,615 B2 | August 2016 | Michaelis et al. | A61B 5/02438 (20130101) |

OTHER PUBLICATIONS

"Cardiac Output", Wikipedia, https://en.wikipedia.org/wiki/Cardiac_output

"Mean Arterial Pressure", Wikipedia, https://en.wikipedia.org/wiki/Mean_arterial_pressure "Metabolic Equivalent", Wikipedia, https://en.wikipedia.org/wiki/Metabolic_equivalent James L. Holly, MD "Aging Well. Part III: Basal Metabolism Rates", Southeast Texas Medical Associates, L.L.P., http://www.setma.com/Your-Life-Your-Health/pdfs/Aging-Well-Part-III.pdf "Basal. Metabolic Rite", Wikipedia, https://en.wikipedia.org/wiki/Basal_metabolic_rate Mifflin, M D; St Jeor, S T; Hill, L A; Scott, B J; Daugherty, S A; Koh, Y O (1990). "A new predictive equation for resting energy expenditure in healthy individuals". The American journal of clinical nutrition 51 (2): 241-7.

"Human Body Weight", Wikipedia, https://en.wikipedia.org/wiki/Human_body_weight

BACKGROUND OF INVENTION

Accurate diagnosis of a personal level of overload activity is required besides obvious sports and medical applications in stressful situations in order to prevent them. Activity estimation is based on the heart rate and there are two major currently existing heart rate monitors HRM: wrist-based and chest-strap. The very earliest technical solutions for placed over the carpal tunnel wrist pulse monitor with infra-red sensor to pick up the flow of blood therein and radio frequency transmitter to transfer data to a display unit which processes it and displays pulse is cited in U.S. Pat. No. 5,810,736 B1. Quite elegant assembly of wrist pulse monitor with additional piezoelectric sensing elements to eliminate power drain from light emitting diode (LED) and thus more complete noise reduction resulting in improved reading accuracy is proposed in U.S. Pat. No. 5,807,267 B1.

A more sophisticated digital apparatus for detecting arrhythmia by analyzing the continuity of change in pulse waveform is suggested in U.S. Pat. No. 6,095,984 B1. Incorporated into device body motion detection means allow accurate arrhythmia monitoring. This device is developed to a higher degree in U.S. Pat. No. 9,597,004 B2 where advanced technological solution allows two-way communication with a server configured and monitored by a cardiologist in case the user initiated the trigger. Device configuration aims constant heart rate and EKG data collection mostly for diagnostic or intense care purposes. Change of patient condition due to aging or new medication prescription requires new appointments and server update. Moreover, amount of volunteers wishing to be monitored by same cardiologist is limited, while provided service could be expensive.

In U.S. Pat. No. 6,580,942 B1 a chest apparatus for detecting an activity of a human heart operates on proposed circuit which analyzes signals received from the sensors and upon determination that such signals are of electrographic nature, i.e. derived from heart beats, generates an alert. This invention is best for patient monitoring before during and after surgical or medical treatment at the hospital. Such an approach is further advanced in U.S. Pat. No. 9,566,007 B2, which proposes a method that is based on a wearable device for continuously and accurately monitoring ECG and photoplethysmograph waveform to determine a patient's vital signs. Wrist and chest detectors comprising an analyzer module and blood pressure measuring by pulse transmit time technique require multiple electrodes attached to the patient's chest. This ultimately restricts the movement capability of the user but makes the device a valuable addition to an operation room.

U.S. Pat. No. 6,042,549 B1 is disclosing a personal device for measuring exercise intensity and quantity based on the user pulse, of which limits are computed and set up from preliminary test of maximum oxygen consumption rate. This method and device is rather for professional athletes undergoing intense training and being observed by qualified medical personnel. A method for monitoring a cardiac status during intense exercise is suggested in U.S. Pat. No. 9,566,010 B2 where the proposed algorithm is based on or related to cardiac output cardio force index normalized to cardiac force index at walking. Such training (or self-training) apparatus functionality fully depends on measured acceleration during walking, input weight of the user, and preset maximum activity level. Unfortunately, definitions of neither acceleration during walking with constant speed, nor individual maximum activity level are specified.

U.S. Pat. No. 9,430,615 B2 depicts a device that goes beyond the scope of a wearable monitor. It is a personal phone that plays music or videos configured to utilize measured by two electrodes EKG signals and monitoring method for detecting heart rate anomalies in the background during use and alerting proper authorities in case irregularity occurs. The shortcoming of the device is that it does not take into account the distinctiveness of each user heart rate based on upon their medical history. Therefore, the definition of "anomaly" is not personal and could result in many false positives.

In general, none of the existing heart rate monitoring devices is capable of predicting personal level of dangerous activity and alarm the user of its approach. Moreover, closely related to pulse issues such as continuous blood pressure and metabolic rate estimations have never been a features of any heart rate monitoring device.

SUMMARY OF INVENTION

Analytically developed method relates instantaneous metabolic and heart rates and targets its application either for a new or existing but paired device capable of measuring individual's pulse.

The proposed method allows evaluation of a personal heart rate and blood pressure at over stressed, or maximum permitted physical or mental activity for an individual of a given build, fit, age, gender medical treatment, and heart rate at rest.

Incorporating the proposed method device(s) with automatically updated or manually reset personal input and instantaneous heart rate can continuously
- compare it with the individual heart rate at maximum activity (over stressed zone) and issues warnings in order to avoid dangerous unhealthy situations;
- estimate and save blood pressure data with the option of transferring it to an authorized party;
- compute user energy consumption and estimate amount of daily weight loss or gain; thus, monitoring three f the most crucial health issues—individual activity, medical conditions, and dieting—have never been presented together in one device suitable for any adult and surely helpful for any physician.

DETAILED DESCRIPTION

A: Definitions

Figure 1A:
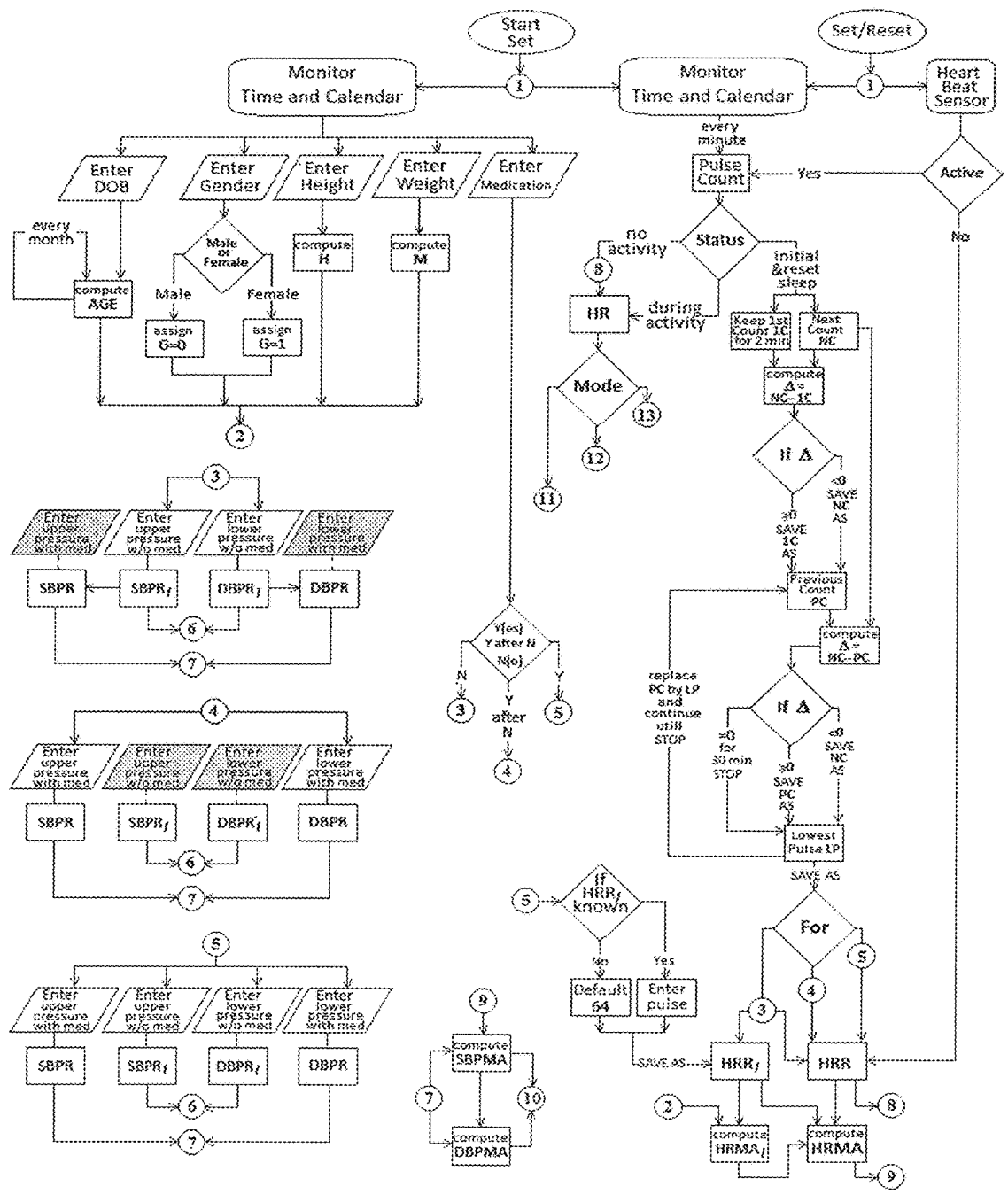
FIG. 1A to 1B. Flow Chart Diagram for continuous diagnosing dangerous and monitoring personal heart rate (activity mode) and blood pressure (personal condition mode) along with the warnings of approaching overstress zone and metabolic rate evaluation (diet mode).
Figure 1B:
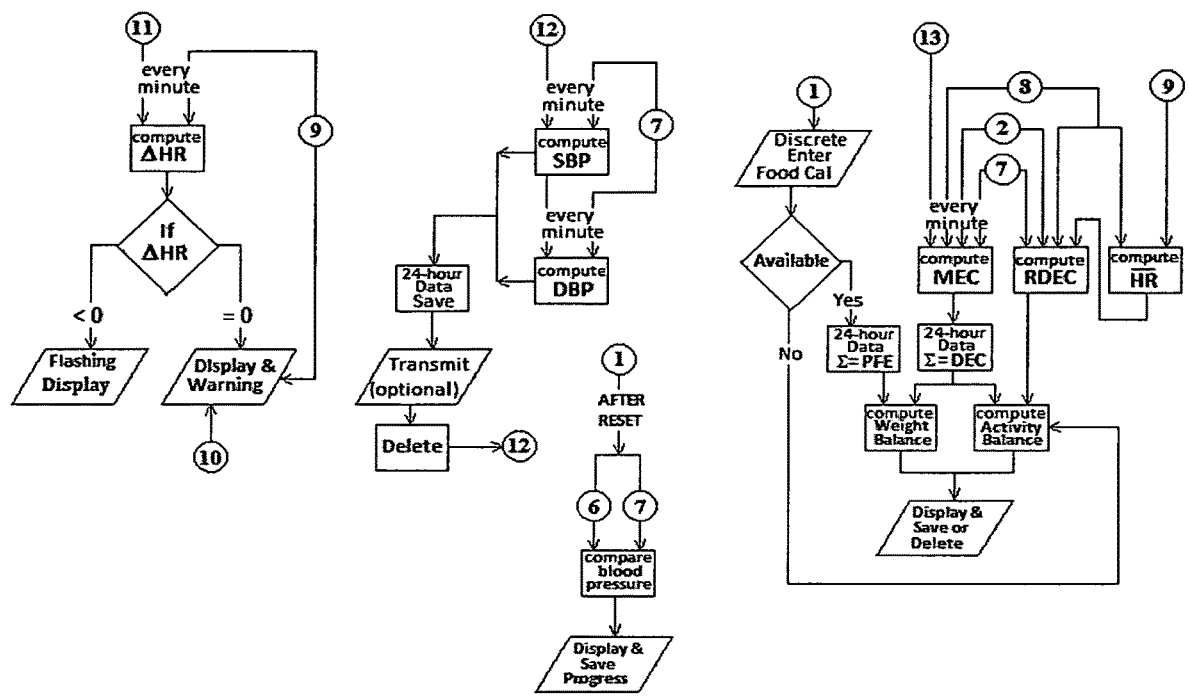

The following definitions are useful in understanding the process of metabolism and its relation to instantaneous heart rate.

HRR is heart rate at rest measured in beat/min;
HRMA is heart rate at maximum allowed activity measured in beat/min;
HR is heart rate at some activity measured in beats/min;
PHRI is percentage of heart rate increase compared to heart rate at rest;
M is mass (weight) of an individual measured in Kg;
IW is ideal weight of an individual measured in Kg;
H is height of the individual measured in m(eters);
AGE is the age of individual measured in y(ears);
MRMA is metabolic rate at maximum allowed activity measured in MET;
PMRMA is personal mean metabolic rate at maximum activity measured in MET;
BMRS is basal metabolic rate standard, measured in Kcal/day;
BMR is individual metabolic rate measure in MET;
SBPR is systolic blood pressure at rest measured in mm Hg;
DBPR is diastolic blood pressure at rest measure in mm Hg;
MAP is mean arterial pressure measured in mm Hg;
CO is cardiac output measured in Liter/min;
R is total peripheral resistance of pulmonary system measured in (mm Hg)*min/Liter;
SV is stroke volume measured in Liter/beat;
G is gender equal +5 for adult male and −161 for an adult female;
A is ideal weight constant equal 50 for male and 45.4 for a female;
PIMR is personal instantaneous metabolic rate measured in Kcal/min
RDEC is required daily energy consumption measured in Kcal/day
PFE is provided by food (and alcohol) energy during the day measured in Kcal/day B: Development of Relevant Solutions In order to function, the body needs energy which is coming from oxygen delivered by blood flow, called cardiac output CO. Hence, energy consumption has to be proportional to cardiac output.

There are two basic equations involving CO:

$$CO = SV * HR \qquad (Eq. 1)$$

$$CO = \frac{MAP}{R} \qquad (Eq. 2)$$

and

Since individual stroke volume SV is a constant parameter and different activities definitely require different cardiac output, energy consumption (or metabolic rate at maximum activity MRMA) according to Eq.1 has to obey proportion $$\frac{MRMA}{PMRMA} = \frac{HRMA}{HRR} \qquad (Eq. 3)$$

Metabolic rate is measured in Metabolic Equivalent of Task (MET) which is a physiological measure expressing the energy cost of physical activities:

$$1 \; MET = 1 \; \frac{Kcal}{kg \cdot hr}$$

| Physical activity | MET |
| --- | --- |
| Light intensity activities | <3 |
| Sleeping | 0.9 |
| watching television | 1.0 |
| writing, desk work, typing | 1.5 |
| walking, 1.7 mph (2.7 km/h), level ground, strolling, very slow | 2.3 |
| walking, 2.5 mph (4 km/h) | 2.9 |
| Moderate intensity activities | 3 to 6 |
| bicycling, stationary, 50 watts, very light effort | 3.0 |
| walking 3.0 mph (4.8 km/h) | 3.3 |
| calisthenics, home exercise, light or moderate effort, general | 3.5 |
| walking 3.4 mph (5.5 km/h) | 3.6 |
| bicycling, <10 mph (16 km/h), leisure, to work or for pleasure | 4.0 |
| bicycling, stationary, 100 watts, light effort | 5.5 |
| sexual activity | 5.8 |
| Vigorous intensity activities | >6 |
| jogging, general | 7.0 |
| calisthenics (e.g. pushups, situps, pullups, jumping jacks), heavy, vigorous effort | 8.0 |
| running jogging, in place | 8.0 |
| rope jumping | 10.0 |

Conservative estimate of dangerous activity MRMA=0.6 MET.

According to James L. Holly, MD the best metabolic rate is observed for adults at the age of 20 with its average reduction by 4% every decade for males and 3% for females for whom metabolic rate is 13% lower than for males.

Further analysis of data presented in this publication reveals the following expression for metabolic rate at maximum activity:

$$MRMA(MET) = \begin{cases} 6*0.96^{\frac{AGE-20}{10}} & \text{for male} \\ 5.2*0.97^{\frac{AGE-20}{10}} & \text{for female} \end{cases} \quad (Eq.\ 4)$$

Personal metabolic rate of an individual PMRMA is the amount of energy the body needs to function at a maximum activity with resting heart rate HRR. PMRMA can be defined from individual metabolic rate BMR which is the number of Kcal required by a given body to support vital functions for the entire day while at rest. The currently accepted standard for basal metabolic rate BMRS of a healthy individual of ideal weight IW is calculated using the Mufflin-St.Jeor equation:

$$BMRS\left(\frac{Kcal}{day}\right) = 10*IW + 625*H - 4.92*AGE + G \quad (Eq.\ 5)$$

Ideal weight divine equation IW(Kg)=$A$+90.55·($H$−1.524)  (Eq.6)

where constant $$A = \begin{cases} 50.0 & \text{for men} \\ 45.5 & \text{for women} \end{cases} \text{ while gender } G = \begin{cases} +5 & \text{for men} \\ -161 & \text{for women} \end{cases}$$

Conversion into metabolic equivalent of task MET reveals expression $$BMRS\ (MET) = \frac{10\cdot[A+90.55\cdot(H-1.524)]+625\cdot H-4.92\cdot AGE+G}{24\cdot[A+90.55\cdot(H-1.524)]} \quad (Eq.\ 7)$$

Normalization of individual metabolic rate BMR to the standard one BMRS (the same person would have in case of being in a perfect health) requires two corrections for:

actual weight M (Kg) leading to coefficient $$\frac{BMR}{DMRS} = \frac{M}{A+90.55-(II-1.524)}$$

and blood pressure (mean arterial blood pressure MAP) which, in assumption of constant peripheral resistance of pulmonary system R and in accordance with Eq.2, provides $$\frac{BMR}{BMRS} = \frac{MAP_{actual}}{MAP_{desired}}$$

In general, mean arterial pressure can be defined as $$MAP = DBPR + 0.01(SBPR - DBPR)\exp\left(4.14 - \frac{40.74}{HR}\right) \quad (Eq.\ 8)$$

For desired blood pressure at 120×80 mm Hg, the second correction coefficient can be defined as $$\frac{BMR}{BMRS} = \frac{DBPR+0.01(SBPR-DBPR)*\exp\left(4.14-\frac{40.74}{HRR}\right)}{80+0.01(120-80)*\exp\left(4.14-\frac{40.74}{HRR}\right)} \quad (Eq.\ 9)$$

Thus, the equation for BMR measured in MET becomes:

$$BMR = M * \frac{10\cdot[A+90.55\cdot(H-1.524)]+625\cdot H-4.92\cdot AGE+G}{24\cdot[A+90.55\cdot(H-1.524)]^2} * \frac{\left[DBPR+0.01(SBRP-DBPR)\cdot\exp\left(4.14-\frac{40.74}{HRR}\right)\right]}{\left[80+0.01(120-80)\cdot\exp\left(4.14-\frac{40.74}{HRR}\right)\right]} \quad (Eq.\ 10)$$

The mean metabolic rate for above average physical work/exercise) PMRMA is usually 2.4 times higher than BMR, or measured in MET $$PMRMA = M * \frac{A+90.55\cdot(H-1.524)+62.5\cdot H-0.492\cdot AGE+0.1\cdot G}{[A+90.55\cdot(H-1.524)]^2} * \frac{DBPR+0.01(SBPR-DBPR)*\exp\left(4.14-\frac{40.74}{HRR}\right)}{80+0.01(120-80)*\exp\left(4.14-\frac{40.74}{HRR}\right)} \quad (Eq.\ 11)$$

Hence, as it follows from Eq.3 dangerous (maximum allowable) heart rate can be evaluated as:

$$HRMA = \frac{6*0.96^{\frac{AGE-20}{10}}*HRR*[80+0.01(120-80)\cdot\exp\left(4.14-\frac{40.74}{HRR}\right)]*[50+90.55\cdot(H-1.524)]^2}{\left[DBPR+0.01(SBPR-DPBR)\cdot\exp\left(4.14-\frac{40.74}{HRR}\right)\right]*[50+90.55\cdot(H-1.524)+62.5\cdot H-0.492\cdot AGE+0.1\cdot 5]\cdot M} \quad (Eq.\ 12a)$$

for men and $$HRMA = \frac{5.2 * 0.97^{\frac{AGE-20}{10}} * HRR * [80 + 0.01(120-80) \cdot \exp\left(4.14 - \frac{40.74}{HRR}\right)] * [45.5 + 90.55 \cdot (H - 1.524)]^2}{[DBPR + 0.01(SBPR - DPBR) \cdot \exp\left(4.14 - \frac{40.74}{HRR}\right)] * [45.5 + 90.55 \cdot (H - 1.524) + 62.5 \cdot H - 0.492 \cdot AGE - 0.1 \cdot 161] \cdot M} \quad (12b)$$

for women.

This equation allows to define percentage of heart rate increase at maximum activity for a person taking no medications for changing blood pressure and pulse $$PHRI = \frac{HRMA - HRR}{HRR} \quad \text{(Eq. 13)}$$

In case medication sets up different heart rate at rest, the limit of dangerous activity should be computed as $$HRMA_{\text{with medication}} = HRR_{\text{with medication}} \cdot \left[1 + \left(\frac{HRMA - HRR}{HRR}\right)_{\text{without medication}}\right] \quad \text{(Eq. 14)}$$

Based on the fact that systolic cycle is two times shorter than the diastolic one there is another expression for mean arterial blood pressure:

$$MAP = DBP + \frac{SBP - DBP}{3} \quad \text{(Eq. 15)}$$

where DBP and SBP are current diastolic and systolic blood pressure respectively.

Hence, Eq.8 and Eq.15 reveal equation $$DBP + \frac{SBP - DBP}{3} = DBPR + 0.01 \cdot (SBPR - DBPR) \cdot \exp\left(4.14 - \frac{40.74}{HR}\right) \quad \text{(Eq. 16)}$$

where HR is heart rate at a given activity

Under the assumption that the ratio of systolic blood pressure to diastolic blood pressure remains the same under any activity $$\frac{SBPR}{DBPR} = \frac{SBP}{DBP}$$

solution of Eq.16 is:

$$SBP = SBPR \cdot \frac{3 + 0.03 \cdot \left(\frac{SBPR}{DBPR} - 1\right) \cdot \exp\left(4.14 - \frac{40.74}{HR}\right)}{\frac{SBPR}{DBPR} + 2} \quad \text{(Eq. 17)}$$

-continued $$DBP = DBPR \cdot \frac{3 + 0.03 \cdot \left(\frac{SBPR}{DBPR} - 1\right) \cdot \exp\left(4.14 - \frac{40.74}{HR}\right)}{\frac{SBPR}{DBPR} + 2}$$

with three related to discussed subject consequences:
State of rest (SBP=SBPR and HR=HRR) does not depend on blood pressure and can be defined as heart rate $$HRR = \frac{40.74}{4.14 + \ln 0.03} \cong 64 \text{ beats/min.}$$

This number, in case no-medication-heart-rate is known or recalled, can be used for computing heart rate at maximum activity in Eqs.12a and 12b and further in Eq.14 for computing maximum allowed heart rate HRMA for a user taken prescription drug;

Pulse is an indicator of blood pressure, of which a dangerous level could be estimated as $$SBPMA = SBPR \cdot \frac{3 + 0.03\left(\frac{SBPR}{DBPR} - 1\right) \cdot \exp\left(4.14 - \frac{40.74}{HRMA}\right)}{\frac{SBPR}{DBPR} + 2} \quad \text{(Eq. 18)}$$

$$DBPMA = SBPMA \cdot \frac{DBPR}{SBPR}$$

Personal instantaneous metabolic rate PIMR, or, measured in Kcal per minute, required for current activity energy, can be estimated by continuously (every minute) monitoring heart rate in accordance with modified Eq.10 as follows $$PIMR = M^2 * \frac{A - 138 + 153.05 \cdot H - 0.492 \cdot AGE + 0.1 \cdot G}{144 \cdot [A + 90.55 \cdot (H - 1.524)]^2} * \frac{\left[DBPR + 0.01(SBPR - DBPR) * \exp\left(4.14 - \frac{40.74}{HR}\right)\right]}{\left[80 + 0.01(120 - 80) * \exp\left(4.14 - \frac{40.74}{HRR}\right)\right]} \quad \text{(Eq. 19)}$$

Replacement of instantaneous heart rate HR in the above equation by daily average heart rate $$\overline{HR} = \frac{HRR + HRMA}{2}$$

leads to evaluation of required daily energy consumption RDEC as $$RDEC = 10 * M^2 * \frac{A - 138 + 153.05 \cdot H - 0.492 \cdot AGE + 0.1 \cdot G}{[A + 90.55 \cdot (H - 1.524)]^2} * \frac{\left[DBPR + 0.01(SBPR - DBPR) * \exp\left(4.14 - \frac{40.74}{\overline{HR}}\right)\right]}{\left[80 + 0.01(120 - 80) * \exp\left(4.14 - \frac{40.74}{HRR}\right)\right]} \quad \text{(Eq. 20)}$$

Further comparison of its value with actually provided by food energy PFE allows to watch over or improve personal diet. On average, carbohydrates (sugars and starches) and proteins provide approximately 4 Kcal/g, lipids (fats) produce 9 Kcal/g, and the oxidation of alcohol produces 7 Kcal/g. Thus, daily balance evaluation could be in favor of gain, loss, or stable weight:

$$\begin{cases} PFE > RDEC \text{ means gaining } \left(\frac{PFE - RDEC}{9}\right) \text{ gramms of fat} \\ RDEC > PFE \text{ means losing } \left(\frac{RDEC - PFE}{9}\right) \text{ gramms of fat} \\ PFE = RDEC \text{ means } \quad\quad \text{breaking even} \end{cases}$$

TABLE

Flow Chart Diagram for Personal Activity, Conditions, and Diet Diagnosing and Monitoring Personal Input
1. Start and Set
2. Input of user at device activation or reset:
   birth date DOB (month, year) converted into $$AGE = \text{current year } \frac{\text{number of current month}}{12} - DOB \text{ year } \frac{\text{number of DOB year month}}{12}$$

automatically updated monthly by adding $\frac{1}{12}$ to former age estimate;

gender (male – female) defined as $G = \begin{cases} 0 & \text{for a male} \\ 1 & \text{for a female} \end{cases}$;

height (Feet – Inches) computed as $H = \frac{\text{Inches} + \text{Feet} * 12}{2.54}$;

weigh (Pounds) computed as $M = 0.453 \cdot \text{Pounds}$ and updated either from the diet output automatically, or from reset manually;
   medical treatment (if medication capable of affecting blood pressure is taken) and blood pressure:
3. If a choice is N(o)
4. If a Y(es) follows previous N(o)
5. If a choice is Y(es)
6. Input of user systolic $SBPR_I$ and diastolic $DBPR_I$ blood pressure at rest without medication in mm Hg
7. Input of user current systolic SBPR and diastolic DBPR blood pressure at rest in mm Hg:
   if medication choice is N(o) then $SBPR_I = SBPR$ and $DBPR_I = DBPR$;
   if medication choice is Y(es) after N(o) then previously input numbers for $SBPR_I$ and $DBPR_I$ remain the same while new input for SBPR and DBPR is required;
   if medication choice is Y(es), then all four numbers known to a user have to be input
8. Estimation of personal heart rate at rest and at maximum activity (overstressed zone):
   The final step of device personalization is wearing it over the sleep time when heart beat sensor keeps the first count 1C and compares it with the next NC defining $\Delta = NC - 1C$. If $\Delta$ is negative or zero then NC is saved as previous count PC, otherwise it is 1C. The whole process is repeated by comparing PC with NC until $\Delta = NC - PC$ remains zero for 30 minutes. The defined lowest pulse LP is user current heart rate at rest HRR.
   It is saved as heart rate at rest without medication $HRR_I$ satisfying choices N(o) and Y(es) after N(o).
   In case of choice Y(es) either manual (if known) or automatic (default 64) input of $HRR_I$ is required.
9. Heart rate at maximum activity without medication is computed as $$HRMA_I = \frac{[6*(1-G)+5.2*G]*[0.96*(1-G)+0.97*G]^{\frac{AGE-20}{10}}*HRR_I * \left\{80+0.4*\exp\left[4.14-\frac{40.74}{HRR_I}\right]\right\}*[50*(1-G)+45.5*G+90.55\cdot(H-1.524)]^2}{\left\{(DBPR)+0.01*[(SBPR)-(DBPR)]*\exp\left[4.14-\frac{40.74}{HRR_I}\right]\right\}*[50*(1-G)+45.5*G+90.55\cdot(H-1.524)+62.5\cdot H-0.492\cdot AGE+0.5*(1-G)-16.1*G]\cdot M}$$

while user current heart rate maximum activity is defined as $HRMA = HRR * \frac{HRMA_I}{HRR_I}$.

| TABLE-continued |
|---|
| Flow Chart Diagram for Personal Activity, Conditions, and Diet Diagnosing and Monitoring |
| 10. Calculation and storage of systolic blood pressure prediction at dangerous activity $$SBPMA = SBPR \cdot \frac{3 + 0.03 \cdot \left(\frac{SBPR}{DBPR} - 1\right) \cdot \exp\left(4.14 - \frac{40.74}{HRMA}\right)}{\frac{SBPR}{DBPR} + 2}$$ Calculation and storage of diastolic blood pressure prediction at dangerous activity $$DBPMA = SBPMA \cdot \frac{DBPR}{SBPR}$$ |
| 1. Reset can be generated automatically or manually with the option to keep or change information of any prompt. Each reset is followed by comparison of systolic and diastolic blood pressure before and after reset in order to evaluate development of health conditions.<br>Personal Output/Monitoring<br>is based on constantly measured instantaneous heart rate HR<br>In case procedure is interrupted HR = HRR. This data is simultaneously used for three monitoring modes: |
| 11. Activity: continuous computation of ΔHR = HRMA − HR. If ΔHR value becomes zero or negative a sound and flashing displayed values of SBP and DBP are activated. |
| 12. Condition: continuous assessment of instantaneous systolic and diastolic blood pressure $$SBP = SBPR \cdot \frac{3 + 0.03\left(\frac{SBPR}{DBPR} - 1\right) \cdot \exp\left(4.14 - \frac{40.74}{HR}\right)}{\frac{SBPR}{DBPR} + 2}$$ $$DBP = SBP \cdot \frac{DBPR}{SBPR}$$ Minutely computed blood pressure is stored in mode memory and accessible upon demand. Every 24 hours all stored data can be transmitted (optional) to a user or authorized party computer and is deleted from the memory. |
| 13. Diet: computed required daily energy consumption $$RDEC = 10 * M^2 * \frac{50*(1-G) + 45.5*G - 138 + 153.05 \cdot H - 0.492 \cdot AGE + 0.5*(1-G) - 16.1*G}{[50*(1-G) + 45.4*G + 90.55 \cdot (H-1.524)]^2} * \frac{\left[DBPR + 0.01(SBPR - DBPR) * \exp\left(4.14 - \frac{40.74}{HR}\right)\right]}{\left[80 + 0.01(120 - 80) * \exp\left(4.14 - \frac{40.74}{HRR}\right)\right]}$$ where daily mean heart rate is defined as $\overline{HR} = \frac{HRR + HRMA}{2}$<br>is compared with daily energy consumption DEC obtained by adding for consequent 24 hours values of minute energy consumption MEC estimated as $$MEC = M^2 * \frac{50*(1-G) + 45.5*G - 138 + 153.05 \cdot H - 0.492 \cdot AGE + 0.5*(1-G) - 16.1*G}{144*[50*(1-G) + 45.5*G + 90.55 \cdot (H-1.524)]^2} * \frac{\left[DBPR + 0.01(SBPR - DBPR) * \exp\left(4.14 - \frac{40.74}{HR}\right)\right]}{\left[80 + 0.01(120 - 80) * \exp\left(4.14 - \frac{40.74}{HRR}\right)\right]}$$ The negative difference (RDEC − DEC) generates the warning of elevated activity on the previous day<br>Optionally this mode might contain an extra input for Provided by Food Energy PFE (in Kcal). In case this option is initiated and used properly, daily weight balance is estimated at the beginning of next cycle as $\frac{PFE - DEC}{4077}$ lbs when positive number means weight gain while a negative one means weight loss.<br>Each new value (positive or negative) has to be added to the previous ones providing with daily diet monitoring and overall result of desired or chosen dieting duration. |

DISCUSSION

Derived process for diagnosing and monitoring individual activity, conditions, and diet is based on established relationship between personal heart beats and true metabolic energy (instead of presently used estimations of mechanical energy) can be efficiently used for upgrading existing or designing new electronic devices capable of:

Estimating expected alarm conditions of dangerous activity by comparing heart rate at rest with the instantaneous one. For randomly-selected individuals "static" analysis reveals trustworthy results.

Automatically updating age information along with changing health conditions affecting heart rate at rest (see table below).
Input new data regarding change of weight, medication taken, and blood pressure.
Predict current and dangerous level of blood pressure.
Monitor energy output (see table below) and compare it with the input (if known) resulting in weight loss or gain.
Further modifications for wireless communications with authorized parties.

While the illustrated embodiment of the invention has been shown and described, numerous variations and alternate embodiments, including eliminating one or more of the steps or elements presented herein, will occur to those skilled in the art. Such variations and alternate embodiments are contemplated and can be made without departing from the spirit and scope of the invention as mentioned in the appended claim.

Estimates of dangerous heart rate level and average daily energy output for randomly chosen individuals

| | Individual | | | | | | | | | | |
|---|---|---|---|---|---|---|---|---|---|---|---|
| | 1 | 2 | 3 | | 4 | | 5 | | 6 | 7 | 8 |
| | w/o med. | w/o med. | w/o med. | with med | w/o med. | with med. | w/o med. | with med. | w/o med. | w/o med. | w/o med. |
| HRR, 1/min | 60 | 70 | (80) | 71 | (64) | 80 | (64) | 75 | 60 | 65 | 65 |
| SBPR, mm Hg | 120 | 145 | (150) | 130 | (160) | 135 | (150) | 130 | 120 | 125 | 125 |
| DBPR, mm Hg | 80 | 80 | (90) | 75 | (110) | 85 | (100) | 80 | 70 | 85 | 80 |
| Weight M, Kg | 70 | 90 | 100 | | 100 | | 80 | | 56 | 60 | 75 |
| Height, H, m | 1.75 | 1.74 | 1.80 | | 1.90 | | 1.68 | | 1.64 | 1.70 | 1.74 |
| AGE, years | 25 | 60 | 65 | | 70 | | 55 | | 60 | 30 | 35 |
| Gender G | male | male | male | | male | | female | | female | female | male |
| HRMA, 1/min | 149 | 117 | (122) | 108 | (97) | 121 | (88) | 103 | 148 | 143 | 111 |
| PHRI, % | — | — | 52.50⬆ | | 51.56⬆ | | 37.5⬆ | | — | — | — |
| High BP, in mm Hg | 127 / 85 | 155 / 86 | 160 / 96 | 138 / 80 | 165 / 113 | 142 / 89 | 154 / 103 | 136 / 84 | 130 / 76 | 132 / 90 | 133 / 85 |
| Average heart rate 4 HR=(HRR+HRMA)/2. | 104 | 94 | (101) | 90 | (80) | 101 | (76) | 89 | 104 | 104 | 104 |
| PIMR, Kcal/min | 1.21 | 1.96 | (2.33) | 1.98 | 2.29 | 1.85 | (1.93) | 1.60 | 0.77 | 0.99 | 1.38 |
| Daily energy required Kcal | 1,735 | 2,825 | (3,355) | 2,855 | (3,298) | 2,664 | (2,775) | 2,305 | 1,110 | 1,425 | 1,990 |

The invention claimed is:

1. A process of controlling a computing device for analytical, reliable, and instantaneous estimate of a personal metabolic rate from heart beats allowing predicting individual limits and evaluating activity, conditions, and diet, said process comprising the following steps:

inputting and assessing individual information from a user at a time, said information comprising:

user date of birth (DOB) input as a birth year number and a birth month number wherein obtaining a current year said device is used (current year number) and a current month said device is used (current month number) a user age (AGE) is assessed:

AGE=current year number−birth year number+(current month number−birth month number)/12;

user gender (G), wherein G=0 when input is male, or G=1 when input is female;

user height number (H) in meters or, if in feet and inches, is calculated with an equation comprising: H=(number of feet*12+number of inches)/39.37;

user weight number (M) in kilograms or, if in pounds, is calculated with an equation comprising: M=0.453*(number of pounds)

a medication taking indication: where yes indicates the user is, at said time, taking medicine that is known to affect blood pressure; or no indicates the user is, at said time, not taking medicine that is known to affect blood pressure;

a systolic blood pressure at rest in mmHg without medication, represented as $SBPR_1$;

a diastolic blood pressure at rest in mmHg without medication, represented as $DBPR_1$;

wherein a SBPR, current systolic blood pressure at rest in mmHg, is equal to $SBPR_1$ if said medication indication is no; or, if said medication indication is changed to yes from a previous medication indication of no, then previous $SBPR_1$ remain unchanged and obtaining said SBPR, or if said medication indication is yes obtaining said SBPR;

wherein a DBPR, current diastolic blood pressure at rest in mmHg, is equal to $DBPR_1$ if said medication indication is no; or, if said medication indication is changed to yes from a previous medication indication of no, then previous $DBPR_1$ remain unchanged and obtaining said DBPR, or if said medication indication is yes obtaining said DBPR;

a value for provided by food energy (PFE) in kilocalories (Kcal) consumed by said user within a preceding 24 hour time period;

personal diagnosing through automatic detection a user heart rate while at rest value (HRR), said HRR obtained, while said user is asleep or at a minimum conscious level of activity, over a time interval of a minimum of 30 minutes, represented as $HRR_1$ value if said medication indication is no and stored to a device memory, and setting $HRR_1=64$ if said medication indication is yes and if no $HRR_1$ value is stored in said device memory, calculating a heart rate at maximum activity ($HRMA_1$) with an equation comprising:

$(HRMA_1)=[6*(1-G)+5.2*G]*[0.96*(1-G)+0.97*G]$
$AGE-20/10*HRR_1*\{80+0.4*exp[4.14-40.74/HRR_1]\}*[50*(1-G)+45.5*G+90.55\cdot(H-1.524)]^2/$
$\{(DBPR)+0.01*[SBPR_1-DBPR_1]*exp[4.14-40.74/HRR_1]\}*[50*(1-G)+45.5*G+90.55\cdot(H-1.524)+62.5\cdot H-0.492\cdot AGE+0.5*(1-G)-16.1*G]\cdot M$ and calculating a present heart rate at maximum activity (HRMA), if said medication indication is yes, with an equation comprising: $HRMA=HRR*HRMA/HRR_1$, or calculating an HRMA, wherein $HRMA=HRMA_1$ if said medication indication is no, defining a daily mean heart rate as $\overline{HR}$, calculated as $\overline{HR}=(HRR+HRMA)/2$;

calculating a systolic blood pressure at maximum activity (SBPMA) with an equation comprising:

$SBPMA=SBPR\cdot 3+0.03\cdot(SBPR/DBPR-1)\cdot exp(4.14-40.74/HRMA)/SBPR/DBPR+2$ and a diastolic blood pressure at maximum activity (DPBMA) with an equation comprising:

$DBPMA=SBPMA\cdot DBPR/SBPR;$ calculating a required daily energy consumption (RDEC) with an equation comprising:

$RDEC=10*M^2*50*(1-G)+45.5*G-138+153.05\cdot H-0.492\cdot AGE+0.5*(1-G)-16.1*G/[50*(1-G)+45.4*G+90.55\cdot(H-1.524)]^2*[DBPR+0.01$
$(SBPR-DBPR)*exp(4.14-40.74/HR)]/[80+0.01(120-80)*exp(4.14-40.74/HRR)];$ continuous monitoring:

automatically detected an instantaneous heart rate value (HR) of said user;

wherein HR is equal to HRR if said automatic detection is interrupted;

outputting to said user an instantaneous activity level, represented continuously as a comparison between said user's HR and HRMA, and notifying said user when $HR\geq HRMA$;

an instantaneous systolic (SBP) and diastolic (DBP) blood pressure value of said user calculated continuously with an equation comprising:

$SBP=SBPR\cdot 3+0.03(SBPR/DBPR-1)\cdot exp(4.14-40.74/HR)/SBPR/DBPR+2;$ and $DBP=SBP\cdot DBPR/SBPR$ an instantaneous per minute energy consumption value (MEC), calculated continuously at minute intervals with an equation comprising:

$MEC=M^2*50(1-G)+45.5*G-138+153.05\cdot H-0.492\cdot AGE+0.5*(1-G)-16.1*G/144*[50*(1-G)+45.5+90.55\cdot(H-1.524)]^2*[DBPR+0.01(SBPR-DBPR)*exp(4.14-40.74/HR)]/[80+0.01(120-80)*exp(4.14-40.74/HRR)]$ summing every MEC value obtained during a 24 hour time period to calculate a daily energy consumption value (DEC), and outputting to said user an instantaneous diet level, represented continuously as a comparison between said user's RDEC and DEC, and notifying said user when DEC>RDEC, calculating a daily weight change value in pounds when said provided by food energy (PFE) value was obtained, said daily weight change value calculated as PFE-DEC/4077, and updating said M value with said daily weight change value.

* * * * *